United States Patent
Wulff et al.

(10) Patent No.: US 6,855,841 B2
(45) Date of Patent: Feb. 15, 2005

(54) PROCESS FOR THE PREPARATION OF N-PHOSPHONOMETHYLGLYCINE

(75) Inventors: Christian Wulff, Manheim (DE); Stefan Orsten, Ellerstadt (DE); Alfred Oftring, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/664,892

(22) Filed: Sep. 22, 2003

(65) Prior Publication Data

US 2004/0063996 A1 Apr. 1, 2004

Related U.S. Application Data

(62) Division of application No. 10/368,577, filed on Feb. 20, 2003, now Pat. No. 6,660,878, which is a division of application No. 10/168,717, filed as application No. PCT/EP00/13162 on Dec. 22, 2000.

(30) Foreign Application Priority Data

Dec. 23, 1999 (DE) .......................................... 199 62 601

(51) Int. Cl.$^7$ ................................................. C07F 9/02
(52) U.S. Cl. ........................ 558/386; 560/174; 562/400
(58) Field of Search ........................ 558/386; 560/174; 562/400; 564/123

(56) References Cited

U.S. PATENT DOCUMENTS

| | | | |
|---|---|---|---|
| 3,459,837 A | * | 8/1969 | Dever et al. .................. 558/89 |
| 3,923,877 A | | 12/1975 | Barton ........................ 260/502 |
| 4,008,296 A | | 2/1977 | Barton ........................ 260/940 |
| 4,053,505 A | | 10/1977 | Dutra ......................... 260/502 |
| 4,067,719 A | | 1/1978 | Dutra ............................. 71/86 |
| 4,083,898 A | | 4/1978 | Dutra ......................... 260/970 |
| 4,089,671 A | | 5/1978 | Dutra ............................. 71/86 |
| 4,181,800 A | | 1/1980 | Kamiya et al. ............. 544/180 |
| 4,415,503 A | | 11/1983 | Robbins ..................... 260/502 |
| 4,429,124 A | | 1/1984 | Felix .......................... 544/214 |
| 4,442,044 A | | 4/1984 | Purdum ..................... 260/969 |
| 4,454,063 A | | 6/1984 | Felix .......................... 260/944 |
| 4,487,724 A | | 12/1984 | Felix .......................... 260/502 |
| 5,053,529 A | | 10/1991 | Ha et al. ...................... 562/18 |

FOREIGN PATENT DOCUMENTS

| | | |
|---|---|---|
| DE | 118 435 | 3/1976 |
| DE | 27 51 631 | 6/1978 |
| DE | 141 929 | 5/1980 |
| EP | 0 097 522 | 1/1984 |
| EP | 0 104 775 | 4/1984 |
| EP | 0 149 294 | 7/1985 |
| EP | 0 164 923 | 12/1985 |

* cited by examiner

*Primary Examiner*—Rita Desai
*Assistant Examiner*—Robert Shiao
(74) *Attorney, Agent, or Firm*—Keil & Weinkauf

(57) ABSTRACT

The present invention relates to a process for the preparation of N-phosphonomethylglycine by reacting a hexahydrotriazine derivative with a triacyl phosphite. The process gives N-phosphonomethylglycine in high yield and in a simple and inexpensive manner.

14 Claims, No Drawings

PROCESS FOR THE PREPARATION OF N-PHOSPHONOMETHYLGLYCINE

This is a application of application Ser. No. 10/368,577, filed Feb. 20, 2003, now U.S. Pat. No. 6,660,878 which is a divisional of application Ser. No. 10/168,717, which file date Jun. 24, 2002 is a 371 of PCT/EP 00/13162 filed on Dec. 22, 2000.

The invention relates to a process for the preparation of N-phosphonomethylglycine by reacting a hexahydrotriazine compound with a triacyl phosphite, and to intermediates for use in this process.

N-Phosphonomethylglycine (glyphosate) is a widely employed nonselective herbicide. A large number of processes for the preparation of phosphonomethylglycine are known. One possibility of preparing it exists in reacting hexahydrotriazine derivatives with phosphorous esters. Thus, U.S. Pat. No. 4,181,800 describes the preparation of hexahydrotriazines of the formula:

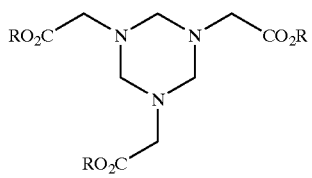

and U.S. Pat. No. 4,053,505 the reaction of these hexahydrotriazines with phosphorous diesters and subsequent hydrolysis of the resulting product to give phosphonomethylglycine. It has emerged that both yield and selectivity favoring the monophosphonated product are capable of improvement. Also, phosphorous diesters are very expensive.

EP-A-104 775 (corresponding to U.S. Pat. Nos. 4,425,284, 4,482,504 and 4,535,181) describes the reaction of the above hexahydrotriazines with an acyl halide and the subsequent phosphonation with a phosphorous triester and hydrolysis to give phosphonomethylglycine in accordance with the following equation:

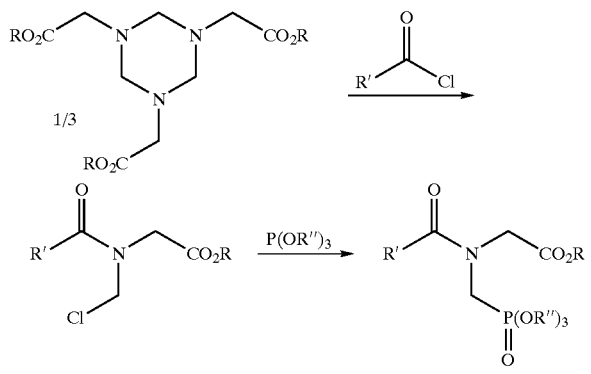

While this process gives relatively good yields of phosphonomethylglycine, it requires not only the use of the expensive phosphorous esters, but additionally the use of carbonyl chloride. In addition, the carbonyl chloride might at most be recovered in the form of the free acid and then reconverted into the acid chloride in a separate step, which considerably increases the costs of the process. Moreover, the alcohol with which the phosphorous acid is esterified cannot be recycled fully since an equivalent of the corresponding alkyl chloride, which is, moreover, toxicologically unacceptable, is formed during the reaction.

U.S. Pat. No. 4,428,888 (corresponding to EP-A-149 294) describes the reaction of the abovementioned hexahydrotriazine with a phosphorous acid chloride in the presence of a strong anhydrous acid, for example hydrogen chloride, and a $C_1-C_6$-carboxylic acid, such as acetic acid. In this manner, a large number of undefined by-products are obtained, and these reduce the phosphonomethylglycine yield and necessitate complicated purification of the product.

U.S. Pat. No. 4,442,044 describes the reaction of a hexahydrotriazine of the formula 5 with a phosphorous acid triester to give the corresponding phosphonate compound, which is used as herbicide.

DD-A-141 929 and DD-A-118 435 describe the reaction of an alkali metal salt of the above hexahydrotriazine (R=for example Na) with a phosphorous diester. However, since alkali salts are sparingly soluble, the conversion rate is only low.

U.S. Pat. No. 5,053,529 describes the preparation of phosphonomethylglycine by reacting the above hexahydrotriazines with phosphorous triesters in the presence of titanium tetrachloride, followed by hydrolysis of the product obtained. The use of titanium tetrachloride makes the preparation considerably more expensive. Moreover, the phosphonomethylglycine yields are unsatisfactory.

U.S. Pat. Nos. 4,454,063, 4,487,724 and 4,429,124 describe the preparation of phosphonomethylglycine by reacting a compound of the formula

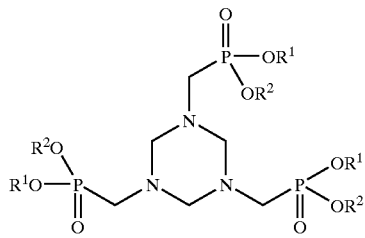

in which $R^1$ and $R^2$ are aromatic or aliphatic groups with RCOX (X=Cl, Br, I) to give a compound of the formula

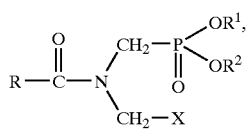

reaction of this product with a metal cyanide and hydrolysis of the product obtained. The disadvantages of this method are stated as above in relation to the use of the acid chloride.

Other possible syntheses which have been described are based on the cyanomethyl-substituted hexahydrotriazine of the formula.

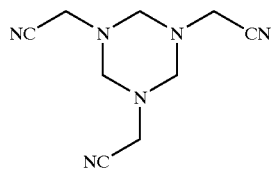

U.S. Pat. Nos. 3,923,877 and 4,008,296 disclose the reaction of this hexahydrotriazine derivative with a dialkyl phosphonate in the presence of an acidic catalyst such as hydrogen chloride, a Lewis acid, a carbonyl chloride or a carboxylic anhydride to give a compound of the formula:

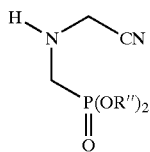

9

Subsequent hydrolysis yields the phosphonomethylglycine, 8 to 10% of the diphosphonomethylated product being formed.

U.S. Pat. Nos. 4,067,719, 4,083,898, 4,089,671 and DE-A-2751631 describe the reaction of cyanomethyl-substituted hexahydrotriazine with a diaryl phosphonate in the absence of a catalyst to give a compound 9 where R″=aryl. This method has the same disadvantages as described above for the use of the carboxyl-substituted hexahydrotriazine 5.

EP-A-097 522 (corresponding to U.S. Pat. Nos. 4,476,063 and 4,534,902) describes the reaction of the hexahydrotriazine 6 with an acyl halide to give 10, the subsequent phosphonation with a phosphorous triester or diester to give 11 and finally the hydrolysis to phosphonomethylglycine as described in the following equation:

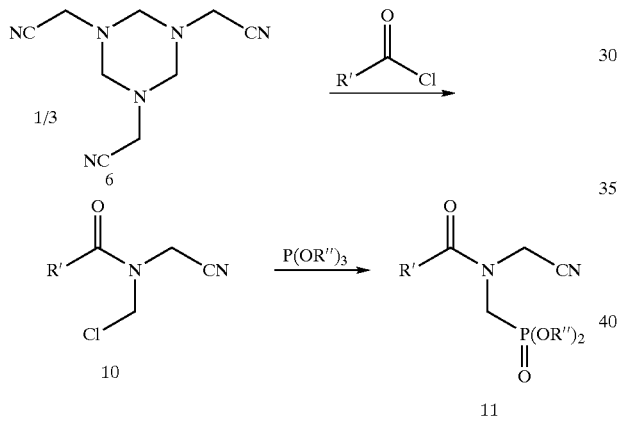

The disadvantages are the same as for the processes in which the carboxyl-substituted hexahydrotriazine derivatives are used.

Finally, U.S. Pat. No. 4,415,503 describes the reaction of the cyanomethyl-substituted hexahydrotriazine in a manner which is similar to the process described in U.S. Pat. No. 4,428,888. Again, substantial formation of by-products can be observed.

EP 164 923 A describes an improved hydrolysis of a compound of the formula 11.

It is an object of the present invention to provide a simple and economical process for the preparation of phosphonomethylglycine in which the phosphomethylglycine is additionally obtained in high purity.

We have found that this object is achieved by reacting a hexahydrotriazine derivative with a triacyl phosphite and subsequently hydrolyzing the product obtained to give phosphonomethylglycine.

The present invention therefore relates to a process for the preparation of N-phosphonomethylglycine, wherein a) a hexahydrotriazine derivative of the formula II

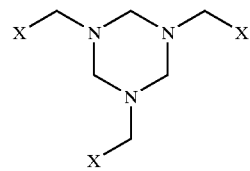

in which X is CN, COOZ, CONR$^1$R$^2$ or CH$_2$OY,

Y is H or a radical which is readily exchangable for H,

Z is H, an alkali metal, alkaline earth metal, C$_1$–C$_{18}$-alkyl or aryl, which is unsubstituted or substituted by C$_1$–C$_4$-alkyl, NO$_2$ or OC$_1$–C$_4$-alkyl, R$^1$ and R$^2$ can be identical or different and are H or C$_1$–C$_4$-alkyl, is reacted with a triacyl phosphite of the formula III

P(OCOR$^3$)$_3$ in which the radicals R$^3$, which can be identical or different, are C$_1$–C$_{18}$-alkyl or aryl which is unsubstituted or substituted by C$_1$–C$_4$-alkyl, NO$_2$ or OC$_1$–C$_4$-alkyl, to give a compound of the formula I

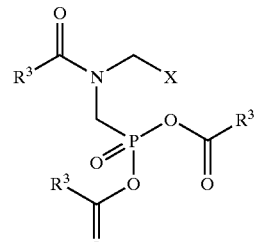

in which R$^3$ and X have the abovementioned meanings and b) the compound of the formula I is hydrolyzed, and, if X is CH$_2$OY, oxidized.

Furthermore, the invention relates to the compounds of the formula I and their preparation in accordance with step a) of the process for the preparation of phosphonomethylglycine.

Alkyl is a linear or branched alkyl chain having preferably 1 to 8 carbon atoms and in particular 1 to 4 carbon atoms. Examples of alkyl are methyl, ethyl, n-propyl, i-propyl, n-butyl, i-butyl, sec-butyl, t-butyl, n-hexyl, 2-ethylhexyl, etc.

Aryl is preferably phenyl and naphthyl.

X is preferably CN or COOZ.

Z is preferably H, alkali metal or C$_1$–C$_{18}$-alkyl.

If Y represents a radical which is readily exchangable for H, this preferably takes the form of an aliphatic or aromatic acyl radical or C$_1$–C$_6$-alkyl group. The aliphatic acyl radical is preferably a C$_1$–C$_6$—CO radical, and the aromatic acyl radical preferably takes the form of the benzoyl radical.

R$^1$ and R$^2$ are preferably H.

The radical R$^3$ especially preferably takes the form of an aryl radical which can be unsubstituted or substituted as stated above. Especially suitable radicals R$^3$ are phenyl, p-tolyl and p-nitrophenyl.

The compounds of the formula II are known and can be prepared in the known manner or analogously to known processes, see, for example, the state of the art mentioned at the outset. For example, an amine X—CH$_2$—NH$_2$ can be reacted with a formaldehyde source, such as aqueous formalin solution or paraformaldehyde, for example by dissolving the primary amine in the aqueous formalin solution. The desired hexahydrotriazine can subsequently be obtained by crystallization or evaporation of the water. This process is described in DE-A-2645085 in accordance with U.S. Pat. No. 4,181,800, whose full extent is referred to herewith.

The compound of the formula II in which X is CN can be obtained by Strecker synthesis, i.e. by reacting ammonia, hydrocyanic acid and a formaldehyde source. Such a process is described, for example, in U.S. Pat. No. 2,823,222, whose full extent is referred to herewith.

The compounds of the formula III can be prepared by a plurality of processes. A first possibility is to react a salt of a carboxylic acid R$^3$COOH with a phosphorus trihalide, in particular phosphorus trichloride. The carboxylate used is preferably an alkali metal salt or alkaline earth metal salt, in particular the sodium, potassium or calcium salt, or the ammonium salt. This reaction can be carried out without using a solvent, and the reaction product obtained can be used directly in step (a). However, the process is preferably carried out in an inert organic solvent, in particular in an ether such as dioxane, tetrahydrofuran and the like, a halogenated, in particular a chlorinated or fluorinated, organic solvent such as dichloromethane, 1,2-dichloroethane, 1,2-dichloropropane, 1,1,1-trichloroethane, 1,1,2-trichloroethane, 1,1,2,2-tetrachloroethane, chlorobenzene or 1,2-dichlorobenzene, an aliphatic or aromatic hydrocarbon such as n-octane, toluene, xylene or nitrobenzene. It is preferred to use the same solvent as subsequently in step (a). Especially preferred is the use of a chlorinated hydrocarbon.

The salt formed during the reaction, for example sodium chloride when using phosphorus trichloride and the sodium salt of the carboxylic acid employed, can be eliminated after the reaction. If ammonium chloride or another ammonium halide is obtained as the salt, the ammonia employed can be recovered by basifying (pH 11–14) an aqueous solution of the salt with a strong base, for example sodium hydroxide solution, and subsequently stripping the ammonia in the customary manner. The ammonia obtained in this manner can be recirculated after drying, for example by distillation in the liquid or gaseous state, or as aqueous solution, and used for preparing the ammonium salt of the carboxylic acid.

Another possibility of preparing the compounds of the formula III is to react a carboxylic acid R$^3$COOH with the phosphorus trihalide in the presence of an amine. Amines which are used are, in particular, aliphatic or cycloaliphatic di- or triamines, such as triethylamine, tributylamine, dimethylethylamine or dimethylcyclohexylamine, and pyridine. In general, such a procedure is carried out in an organic solvent. Suitable solvents are stated above in connection with the first possibility for preparation. Dioxane, 1,2-dichloropropane, 1,2-dichloroethane, nitrobenzene or toluene are preferably used. When using a solvent, the amine hydrochloride formed precipitates and can be removed by filtration. If the amine hydrochlorides are treated with a strong base, for example with aqueous sodium hydroxide solution, the amines are set free from the hydrochloride. Volatile amines can then be recovered by distillation or extraction. Nonvolatile amines can be recovered by extraction or, if a two-phase mixture is obtained when the amine is set free, by phase separation. Solid amines can be recovered by filtration. The amines recovered can be recirculated into the process, if appropriate after drying.

Another possibility of preparing the compounds of the formula III is to react the carboxylic acid R$^3$COOH with a phosphorus trihalide, in particular phosphorus trichloride, without addition of a base. In this reaction, the hydrogen halide which forms must be removed from the reaction mixture. This can be done in the customary fashion, for example by passing through an inert gas, such as nitrogen. The hydrogen halide which has been set free can then be used for the hydrolysis in step (b) in the form of an aqueous solution.

Step (a) of the process according to the invention can be carried out with or without solvent, for example in the melt. However, it is preferred to use an inert organic solvent, for example a hydrocarbon such as toluene or xylene, an ether such as tetrahydrofuran, dioxane or dibutyl ether, nitrobenzene and the like. It is especially preferred to carry out the process in a halogenated solvent, in particular a chlorinated, preferably a chlorinated and/or fluorinated aliphatic hydrocarbon, such as dichloromethane, 1,2-dichloroethane, 1,2-dichloropropane, 1,1,1-trichloroethane, 1,1,2-trichloroethane, 1,1,2,2-tetrachloroethane, chlorobenzene or 1,2-dichlorobenzene. The reactants are expediently employed in essentially stoichiometric amounts. However, an excess of, for example, up to 10% of one or the other reactant may also be used. In general, the reaction temperature is in the range of –10° C. to 140° C., preferably in the range of room temperature to 100° C. Only short reaction times are required under these conditions; in general, the reaction is essentially complete after 10 to 30 minutes.

The compounds of the formula I obtained in accordance with step (a) are useful intermediates for preparing phosphonomethylglycine. To this end, the compounds of the formula I are hydrolyzed. The hydrolysis can take the form of an acid or alkaline hydrolysis, preferably an acid hydrolysis. Acids which are used are, in particular, inorganic acids such as hydrochloric acid, sulfuric acid or phosphoric acid. Alkaline hydrolysis is generally carried out using an alkali metal hydroxide or alkaline earth metal hydroxide, in particular using sodium hydroxide or potassium hydroxide.

The hydrolysis is expediently carried out with an aqueous acid or base. In general, the aqueous acid or base is added to the reaction mixture obtained in step (a). The hydrolysis can be carried out without solvent or in the presence of an inert organic solvent which is fully or in part or not miscible with water. The solvent employed in step (a) is preferably used. When using a solvent in step (a), the reaction mixture obtained in step (a) is expediently employed directly, if appropriate after removing, for example by distillation, some of the solvent. As an alternative, the solvent used in step (a) is removed completely and the residue is hydrolyzed. The solvent recovered from the reaction mixture can be reused in the preparation of the compounds of the formula III or in step (a).

It is especially preferred to carry out the hydrolysis in a two-phase system (aqueous phase/organic phase). Here, an organic solvent which is miscible in part with water or not miscible with water is used, preferably a hydrocarbon such as toluene or xylene, an ether such as dibutyl ether and in particular a halogenated hydrocarbon such as stated above as solvent for step (a). Hydrolysis is carried out with intimate mixing of the two phases using customary devices, for example stirred reactors, circulating reactors or, preferably, static mixers. After hydrolysis has ended, the phases are separated and processed as described below.

An especially preferred embodiment is a process in which step (a) is carried out in a halogenated solvent, some of the solvent is removed, if appropriate, and the resulting compound of the formula I is hydrolyzed by treating the reaction mixture obtained in step (a) with an aqueous acid or base.

As an alternative, the compound of the formula I can also be hydrolyzed into phosphonomethylglycine by enzymatic means, for example using an esterase or a nitrilase.

The acid or base is used in at least equivalent amounts, but preferably in excess, in particular in an amount of $\geq 2$ equivalents.

The temperature at which the hydrolysis is carried out is generally in the range of approximately 10° C. to 180° C., preferably 20 to 150° C.

If X is $CH_2OY$, the product obtained after hydrolysis still requires oxidation. The starting compound is, in particular, one in which X is $CH_2OH$. The oxidation to give phosphonomethylglycine is carried out in the customary manner which is known to the skilled worker, for example by catalytic dehydration with copper catalysis.

If X is $CH_2OY$ and Y is an acyl radical, hydrolysis of the product of step a) involves elimination of the acyl radical with formation of the corresponding compound where $X=CH_2OH$. This is oxidized as stated above to give phosphonomethylglycine.

If X is $CH_2OY$ and Y is an alkyl radical, ether cleavage normally takes place simultaneously under the conditions of an acid hydrolysis of the product of step a). The compound obtained where $X=CH_2OH$ is oxidized as stated above to give phosphonomethylglycine.

The phosphonomethylglycine obtained when hydrolyzing using an excess of acid or base is dissolved in the aqueous phase. The carboxylic acid $R^3COOH$ is formed directly when hydrolyzing with an excess of acid or, when hydrolyzing with a base, after acidification with a strong acid, preferably to a pH of <0.5. The carboxylic acid is then removed in the customary manner, for example by filtration of the carboxylic acid which has precipitated in solid form, distillation or extraction with an organic solvent which is not miscible with the aqueous phase. If hydrolysis is biphasic, the carboxylic acid is present in dissolved form in the organic phase, if appropriate. The carboxylic acid is then removed by separating off the organic phase and, if desired, can be recovered therefrom in the customary manner. It is obtained in high purity and can be recycled without problems for the preparation of the compound of the formula III. The solvent which forms the organic phase can be recirculated and reused in the preparation of the compounds of the formula III or in step (a). In general, however, the solvent is previously subjected to distillation, extraction, filtration and/or stripping in order to remove contaminants such as alcohols, phenols, ammonium salts and/or carboxylic acids which are soluble or insoluble in water.

The phosphonomethylglycine can be precipitated by bringing the aqueous phase to a pH in the region of 0.5 to 2.0, in particular 0.8 to 1.5, for example by adding an acid or base, for example HCl, $H_2SO_4$ or NaOH, KOH, $Ca(OH)_2$ and obtained in the customary manner, if appropriate by concentrating the aqueous phase and/or addition of a precipitant, for example by filtration. A solvent which is miscible with water, such as methanol, ethanol, isopropanol, acetone and the like, is preferably used as precipitant. The solvents can be recovered from the mother liquor by distillation and reused.

Ammonia or ammonium chloride formed during the hydrolysis can be recirculated into the process, if appropriate by basifying the mixture and recovering the ammonia by stripping.

If required, the phosphonomethylglycine obtained can be decolorized in the customary manner. This can be done for example by treating it with small amounts of a decolorizing agent, for example oxidants such as perborates or $H_2O_2$ or adsorbents such as active charcoal. The amount of decolorizing agent depends on the degree of the discoloration and can be determined in a simple manner by the skilled worker. The treatment with the decolorizing agent can be performed at any point after hydrolysis and in the customary manner. It is expedient to add the decolorizing agent before precipitating the phosphonomethylglycine.

The process according to the invention, or each step on its own, can be carried out continuously, discontinuously or as a semi-batch process. Reaction vessels which are customary for such purposes are used, such as stirred reactors or tubular reactors, if appropriate with mixing devices arranged upstream or with mixing elements integrated into the tubular reactor.

The process according to the invention is thus distinguished by simple process control and inexpensive feed stocks. Only an inorganic chloride is produced as waste product, and the protective groups, viz. the actyl radicals of the triacyl phosphite of the formula III, can be recycled in a simple manner. The process yields phosphonomethylglycine in very short reaction times and high yields of >90% of hexahydrotriazine of the formula II.

The examples which follow illustrate the invention without imposing any limitation.

EXAMPLE 1

0.2 mol of sodium benzoate are introduced into 50 ml of 1,4-dioxane at room temperature with the exclusion of moisture. 0.0667 mol of phosphorous trichloride are added dropwise, and stirring of the reaction is continued for 20 minutes at 85° C. (colorless suspension). 0.0222 mol of the hexahydrotriazine 6 are added, and the reaction is stirred for a further 20 minutes at 85 to 90° C. (thin suspension, readily stirrable). The dioxane is subsequently distilled off in vacuo at 40° C. 100 ml of concentrated hydrochloric acid are added to the residue and the mixture is refluxed for 4 hours. After cooling, the benzoic acid is filtered off, washed (with a little cold water) and dried.

The combined filtrates are evaporated to dryness. To isolate the phosphonomethylglycine, the residue is taken up in a little water and precipitated by adding cold NaOH to pH=1.5. Complete precipitation is achieved by adding a little methanol. The phosphonomethylglycine is filtered off and dried.

Yield: 10.3 g of phosphonomethylglycine (purity 95.3% according to HPLC), corresponding to 91% yield based on $PCl_3$. The crystallization mother liquor still contains 1.8% by weight of phosphonomethylglycine.

EXAMPLE 2

0.2 mol of sodium benzoate are introduced into 50 ml of 1,4-dioxane at room temperature with the exclusion of moisture. 0.0667 mol of phosphorous trichloride are added dropwise, and stirring of the reaction is continued for 20 minutes at 85° C. (colorless suspension). The reaction is filtered with the exclusion of moisture and the residue is washed with a little dixoane. 0.0222 mol of the hexahydrotriazine 6 are added to the filtrate, still with exclusion of moisture, and the reaction is stirred for a further 20 minutes at 85 to 90° C. The dioxane is subsequently distilled off in vacuo at 40° C. 100 ml of concentrated hydrochloric acid are added to the residue and the mixture is refluxed for 4 hours. After cooling, the benzoic acid is filtered off, washed (with a little cold water) and dried.

The combined filtrates are evaporated to dryness. To isolate the phosphonomethylglycine, the residue is taken up in a little water and precipitated by adding cold NaOH to pH=1.5. Complete precipitation is achieved by adding a little methanol. The phosphonomethylglycine is filtered off and dried.

Yield: 10.5 g of phosphonomethylglycine (purity 94.1% according to HPLC), corresponding to 93% yield based on $PCl_3$. The crystallization mother liquor still contains 1.9% by weight of phosphonomethylglycine.

EXAMPLE 3

A solution of 0.12 mol of triacetyl phosphite in 50 ml of dioxane is added at room temperature to a solution of 0.04 mol of the hexahydrotriazine 6 in 80 ml of dioxane. Stirring of the solution is continued for 2 hours at 100° C. The solvent is subsequently distilled off at 40° C., first under atmospheric pressure and then in vacuo. 100 ml of concentrated hydrochloric acid are added to the residue and the reaction is refluxed for 4 hours. The reaction mixture is evaporated to dryness. To isolate the phosphonomethylglycine, the residue is taken up in a little water and precipitated by adding cold NaOH to pH=1.5. Complete precipitation is achieved by adding a little methanol. The phosphonomethylglycine is filtered off and dried.

Yield: 15.4 g of phosphonomethylglycine (purity 98.7% according to HPLC), corresponding to 76% yield based on $PCl_3$. The crystallization mother liquor still contains 1.6% by weight of phosphonomethylglycine.

EXAMPLE 4

284 g of ammonium benzoate in 1000 ml of 1,2-dichloroethane are introduced into a stirred 2-1-flask equipped with a teflon blade mixer and a reflux condenser, and 91.5 g of phosphorus trichloride are added dropwise under a nitrogen atmosphere in the course of 30 minutes. During this, the temperature climbs to a maximum of 36° C. Stirring is subsequently continued for 30 minutes at 25 to 36° C. The mixture is filtered through a pressure filter, and the filter cake is washed twice more with two 500 g portions of dichloroethane under nitrogen (2054 g of filtrate).

The filtrate is introduced at room temperature into a stirred 2-1-flask equipped with a teflon blade mixer and a reflux condenser. The stirred filtrate is heated to 80° C. in the course of 30 minutes, and stirring is continued for 30 minutes at 80° C. The solution is left to cool and is hydrolyzed directely thereafter.

To this end, the feedstock is metered at 130° C. and 8 bar into a tubular reactor (approx. volume 600 ml) with a static mixer arranged upstream (1265 g/h of the dichloroethane solution from the preceding step, 207 g/h 20% strength HCl). The residence time is 30 minutes. The first runnings are discarded. For processing, the resulting two-phase mixture is collected for 60 minutes. The phases are separated at 60° C. and the aqueous phase is extracted twice with two 100 g portions of dichloroethane.

The dichloroethane, which is still present in the aqueous phase, is first stripped at 60° C. in a round-bottomed flask equipped with a teflon blade stirrer by passing in nitrogen. Then, the pH is brought to 1.0 at 40 to 60° C. in the course of 15 minutes, using 50% strength sodium hydroxide solution. Stirring of the resulting suspension is continued for 3 hours at 40° C., the mixture is left to cool to room temperature, and the product which has precipitated is filtered off with suction and subsequently washed with 150 g of ice-water. The resulting solid is dried for 16 hours at 70° C. and 50 mbar.

Yield: 54.6 g of phosphonomethylglycine (purity according to HPLC: 96.2%), which corresponds to 80% yield based on $PCl_3$. The crystallization mother liquor still contains 2.1% by weight of phosphonomethylglycine.

EXAMPLE 5

A saturated solution in water is prepared from the ammonium chloride residue of the tribenzoyl phosphite synthesis as described in Example 4. This saturated solution is combined with the mother liquor from the crystallization of the phosphonomethylglycine as described in Example 4 and brought to pH 14 with excess sodium hydroxide solution. Then, ammonia is stripped from the reaction mixture using nitrogen and collected for gas analysis by means of GC (purity 99%). The combined dichloroethane phases from the hydrolysis are dried by distilling off the azeotrope dichloroethane/water. Dry ammonia is passed into the dichloroethane until all of the benzoic acid has been reacted to give ammonium benzoate, and the resulting suspension of ammonium benzoate in 1,2-dichloroethane is returned into the synthetic procedure.

Yield (first recycling): 54.0 g of phosphonomethylglycine (purity 97.0% according to HPLC) corresponds to 79% yield based on $PCl_3$.

Yield (second recycling): 55.1 g of phosphonomethylglycine (purity 95.5% according to HPLC) corresponds to 81% yield based on $PCl_3$.

EXAMPLE 6

The reaction is carried out as described in Example 4, except that nitrobenzene is used as solvent instead of 1,2-dichloromethane.

Yield: 56.2 g of phosphonomethylglycine (purity according to HPLC: 97.4%), which corresponds to 82% yield based on $PCl_3$. The crystallization mother liquor still contains 2.0% by weight of phosphonomethylglycine.

EXAMPLE 7

The reaction is carried out as described in Example 4, except that 1,2-dichloropropane is used as solvent instead of 1,2-dichloroethane.

Yield: 54.0 g of phosphonomethylglycine (purity according to HPLC: 96.92%), which corresponds to 79% yield based on $PCl_3$. The crystallization mother liquor still contains 2.1% by weight of phosphonomethylglycine.

EXAMPLE 8

The reaction is carried out as described in Example 1, except that 1,2-dichloroethane is used as solvent instead of dioxane. The phosphonomethylglycine yield is 75%.

EXAMPLE 9

The reaction is carried out as described in Example 1, except that toluene is used as solvent instead of dioxane. The phosphonomethylglycine yield is 68%.

EXAMPLE 10

Preparation of the Phosphite from Carboxylic Acid, Amine and $PCl_3$ 0.05 mol of phosphorus trichloride in 15 ml of toluene is added dropwise at 0° C. to a solution of 0.15 mol of benzoic acid and 0.15 mol of dimethylcyclohexylamine in 90 ml of toluene. Stirring is continued for 15 minutes at 0° C. and the mixture is subsequently allowed to come to room temperature. The hydrochloride which has precipitated is filtered through a pressure filter with exclusion of moisture. The tribenzoyl phosphite is characterized via analysis of the filtrate by $^1$H NMR and $^{31}$P NMR (yield: 99%). If the residue obtained from the filtrate after the toluene has been distilled off is added to 0.15 mol of 10% strength NaOH, dimethylcyclohexylamine can be recovered quantitatively by phase separation followed by extraction with toluene. The solution is subsequently dried by removing the water azeotropically and can be reused.

EXAMPLE 11

0.2 mol of sodium benzoate are added to 50 ml of 1,4-dioxane at room temperature with exclusion of moisture. 0.0667 mol of phosphorus trichloride is added dropwise and stirring of the mixture is continued for 20 minutes at 85° C. (colorless suspension). 0.0222 mol of the hexahydrotriazine 1 (X=CN) is added, and stirring of the mixture is continued for another 20 minutes at 85–90° C. (thin suspension, readily stirrable). The dioxane is subsequently distilled off in vacuo at 40° C. 100 ml of concentrated hydrochloric acid are added to the residue and the mixture is refluxed for 4 hours. When cold, the benzoic acid is filtered off and washed (a little cold water). The combined filtrates are extracted twice with in each case 30 ml of toluene, evaporated to dryness on a rotary evaporator and rotary-evaporated three more times with ethanol to remove excess hydrochloric acid. The toluene phase is concentrated and the residue is combined with the benzoic acid which has been recovered.

To isolate the phosphonomethylglycine from the residue of the aqueous phase, this may now be taken up in a little water and precipitated cold at pH 1.0 (addition of NaOH). Complete precipitation is achieved by adding a little methanol, which is recovered from the mother liquor by distillation. Yield: 91%.

The benzoic acid which has been recovered (0.2 mol, purity >99% according to HPLC) is dissolved in 0.2 mol of 5% strength NaOH, the water is subsequently distilled off and the residue is dried. The resulting sodium benzoate together with the dioxane which has been recovered is reused in the synthetic procedure.
Yield (first recycling): 90%
Yield (second recycling): 84%
Yield (third recycling): 88%.

We claim:

1. A process for the preparation of a phosphono tcompound of the formula I

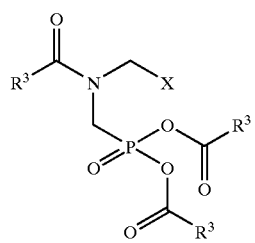

(I)

in which the radicals R$^3$, which can be identical or different, are C$_1$–C$_{18}$-alkyl or aryl which is unsubstituted or substituted by C$_1$–C$_4$-alkyl, NO$_2$ or OC$_1$–C$_4$-alkyl, and X is CN, COOZ, CONR$^1$R$^2$ or CH$_2$OY, Y is H or is a radical which is readily exchangeable for H selected from the group consisting of C$_1$–C$_6$-alkyl, aliphatic acyl having a C$_1$–C$_6$ aliphatic group, and benzoyl;

Z is H, an alkali metal, alkaline earth metal, C$_1$–C$_{18}$-alkyl or aryl, which is unsubstituted or substituted by C$_1$–C$_4$-alkyl, NO$_2$ or OC$_1$–C$_4$-alkyl;

R$^1$ and R$^2$, which can be identical or different, are H or C$_1$–C$_4$-alkyl, in which a hexahydrotriazine derivative of the formula II

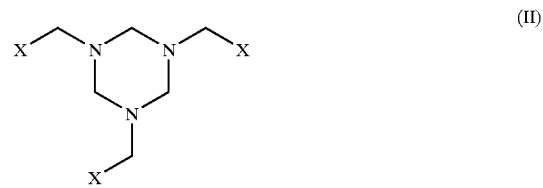

(II)

is reacted with a triacyl phosphite of the formula II $$P(OCOR^3)_3 \quad \quad (III)$$

in which R$^3$ and X are as defined above.

2. A process as claimed in claim 1, wherein X is CN or COOZ.

3. A process as claimed in claim 1, wherein R$^3$ is phenyl which is unsubstituted or substituted by C$_1$–C$_4$-alkyl, NO$_2$ or OC$_1$–C$_4$-alkyl, or is CH$_3$.

4. A process as claimed in claim 1, which is carried out in an organic solvent.

5. A process as claimed in claim 4, wherein the solvent is dioxane or tetrahydrofurane.

6. A process as claimed in claim 4, wherein a chlorinated organic solvent is used.

7. A process as claimed in claim 6, wherein 1,2-dichloroethane is used as solvent.

8. A process as claimed in claim 1, wherein the compounds of the formulae II and III are employed in essentially equivalent amounts.

9. A process as claimed in claim 1, which further comprises preparing the compound of the formula III by reacting a carboxylic acid of the formula IV $$R^3COOH \quad \quad (IV),$$

in which R$^3$ has the meanings stated in claim 3 or a salt thereof with a phosphorus trihalide.

10. A process as claimed in claim 9, wherein an alkali metal salt or the ammonium salt of the carboxylic acid of the formula IV is reacted with the phosphorus halide.

11. A process as claimed in claim 9, wherein the carboxylic acid of the formula IV is reacted with the phosphorus halide in the presence of an amine.

12. A process as claimed in claim 9, wherein the carboxylic acid of the formula IV is reacted with the phosphorus halide in the absence of a base.

13. A process as claimed in claim 9, wherein the reaction is carried out in an inert organic solvent which is selected from among the aromatic or aliphatic hydrocarbons and chlorinated hydrocarbons.

14. A process as claimed in claim 13, wherein the solvent is recovered after the reaction and recycled.

* * * * *

UNITED STATES PATENT AND TRADEMARK OFFICE
CERTIFICATE OF CORRECTION

PATENT NO. : 6,855,841 B2 Page 1 of 1
APPLICATION NO. : 10/664892
DATED : February 15, 2005
INVENTOR(S) : Christian Wulff et al.

It is certified that error appears in the above-identified patent and that said Letters Patent is hereby corrected as shown below:

Claim 1, column 12, line 23, "formulaII" should read --formula III--.

Signed and Sealed this

First Day of August, 2006

JON W. DUDAS
*Director of the United States Patent and Trademark Office*